US012011269B2

(12) United States Patent
Rundo et al.

(10) Patent No.: US 12,011,269 B2
(45) Date of Patent: Jun. 18, 2024

(54) ELECTROPHYSIOLOGICAL SIGNAL PROCESSING METHOD, CORRESPONDING SYSTEM, COMPUTER PROGRAM PRODUCT AND VEHICLE

(71) Applicant: STMicroelectronics S.r.l., Agrate Brianza (IT)

(72) Inventors: Francesco Rundo, Gravina di Catania (IT); Sabrina Conoci, Tremestieri Etneo (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 697 days.

(21) Appl. No.: 16/819,688

(22) Filed: Mar. 16, 2020

(65) Prior Publication Data

US 2020/0330020 A1 Oct. 22, 2020

(30) Foreign Application Priority Data

Apr. 16, 2019 (IT) .......................... 102019000005868

(51) Int. Cl.
*G06F 7/00* (2006.01)
*A61B 5/00* (2006.01)
(Continued)

(52) U.S. Cl.
CPC ............... *A61B 5/18* (2013.01); *A61B 5/316* (2021.01); *A61B 5/725* (2013.01); *A61B 5/7264* (2013.01);
(Continued)

(58) Field of Classification Search
CPC ........... A61B 5/18; A61B 5/316; A61B 5/725; A61B 5/7264; A61B 5/746;
(Continued)

(56) References Cited

U.S. PATENT DOCUMENTS 10,650,824 B1 5/2020 Kesharaju et al.
2008/0101512 A1 5/2008 Mohamed et al.
(Continued)

FOREIGN PATENT DOCUMENTS

GB 2570535 A 7/2019
WO 2004107963 A2 12/2004

OTHER PUBLICATIONS

B.-G. Lee, et al., "Real-time physiological and vision monitoring of vehicle driver for non-intrusive drowsiness detection," IET Communications, 2011, vol. 5, Issue: 17, 9 pages.
(Continued)

*Primary Examiner* — Naomi J Small
(74) *Attorney, Agent, or Firm* — Slater Matsil, LLP

(57) ABSTRACT

In an embodiment, a method of processing an electrophysiological signal includes collecting the electrophysiological signal that is indicative of a level of attention of a human; filtering the electrophysiological signal via joint low-pass and high-pass filtering using a set of filtering parameters including low-pass filters parameters and high-pass filters parameters having a set of low-pass cut-off frequencies and a set of high-pass cut-off frequencies respectively. The method further includes applying artificial neural network processing to the filtered electrophysiological signal to extract therefrom a set of features of the electrophysiological signal. The method further includes applying classifier processing to the set of features extracted from the filtered electrophysiological signal and producing a classification signal indicative of the level of attention of the human. The method further includes generating a trigger signal to trigger a user circuit based on the classification signal.

21 Claims, 9 Drawing Sheets

(51) Int. Cl.
 A61B 5/18 (2006.01)
 A61B 5/316 (2021.01)
 B60W 40/08 (2012.01)
(52) U.S. Cl.
 CPC .............. *A61B 5/746* (2013.01); *B60W 40/08* (2013.01); *A61B 2560/0228* (2013.01); *B60W 2040/0872* (2013.01)
(58) Field of Classification Search
 CPC .......... A61B 2560/0228; B60W 40/08; B60W 2040/0872
 USPC .......................................................... 701/36
 See application file for complete search history.

(56) References Cited

U.S. PATENT DOCUMENTS

| | | | |
|---|---|---|---|
| 2008/0103403 A1* | 5/2008 | Cohen | G16H 50/20 600/509 |
| 2010/0042172 A1 | 2/2010 | Armoundas | |
| 2012/0123232 A1 | 5/2012 | Najarian et al. | |
| 2015/0257668 A1 | 9/2015 | Braojos Lopez et al. | |
| 2016/0001781 A1* | 1/2016 | Fung | G07C 9/37 701/36 |
| 2016/0183812 A1 | 6/2016 | Zhang et al. | |
| 2016/0345907 A1* | 12/2016 | Fung | A61B 5/14552 |
| 2017/0267251 A1* | 9/2017 | Roberts | G08B 21/06 |
| 2018/0214088 A1 | 8/2018 | Newberry | |
| 2018/0249960 A1* | 9/2018 | Gupta | A61B 5/318 |
| 2018/0330178 A1 | 11/2018 | el Kaliouby et al. | |
| 2019/0021615 A1* | 1/2019 | Rundo | A61B 5/725 |
| 2019/0099118 A1* | 4/2019 | Patel | A61B 5/746 |
| 2019/0117096 A1* | 4/2019 | Rundo | A61B 5/02405 |
| 2019/0156934 A1* | 5/2019 | Kataoka | G16H 40/63 |
| 2019/0159735 A1* | 5/2019 | Rundo | A61B 5/725 |
| 2019/0166122 A1 | 5/2019 | Mochizuki et al. | |
| 2020/0156648 A1* | 5/2020 | Zhang | B60W 40/08 |
| 2020/0285873 A1 | 9/2020 | Condon | |
| 2020/0324784 A1 | 10/2020 | Liang et al. | |
| 2020/0330020 A1 | 10/2020 | Rundo et al. | |

OTHER PUBLICATIONS

Bolanos, M., et al., "Comparison of heart rate variability signal features derived from electrocardiography and photoplethysmography in healthy individuals", Proceedings of the 28th IEEE EMBS Annual International Conference, New York City, USA, Aug. 30-Sep. 3, 2006, 6 pages.
Deepu Kurian, et al., "Drowsiness Detection Using Photoplethysmography Signal," 2014 Fourth International Conference on Advances in Computing and Communications Year: 2014, 4 pages.
Gi-Seong Ryu, et al., "Flexible and Printed PPG Sensors for Estimation of Drowsiness," IEEE Transactions on Electron Devices, vol. 65, No. 7, Year: 2018, 8 pages.
Nila Novita Sari, et al., "A two-stage intelligent model to extract features from PPG for drowsiness detection," 2016 International Conference on System Science and Engineering (ICSSE) Year: 2016, 2 pages.
Vala Jeyhani, et al., "Comparison of HRV parameters derived from photoplethysmography and electrocardiography signals", 2015 37th Annual International Conference of the IEEE Engineering in Medicine and Biology Society (EMBC) Year: 2015, 4 pages.
Vicente, Jose, et al., "Detection of Driver's Drowsiness by means of HRV Analysis", IEEE Computing in Cardiology, 2011; 38, 4 pages.
Agro, D., et al. "PPG Embedded System for Blood Pressure Monitoring", AEIT Annual Conference—From Research to Industry: The Need for a More Effective Technology Transfer (AEIT), Trieste, Sep. 18-19, 2014, 6 pages.
Wikipedia, "Dynamic time warping", Aug. 20, 2019, 7 pages, retrieved from https://en.wikipedia.org/w/index.php?title=Dynamic_time_warping&oldid=911733837 (retrieved on May 4, 2020).
Wikipedia, "Sofmax function", Sep. 2, 2019, 8 pages, retrieved from https://en.wikipedia.org/w/index.php?title=Softmax_function&oldid=913685380 (retrieved on May 4, 2020).
Bengio, Yoshua, "Learning Deep Architectures for AI", Foundations and Trends® in Machine Learning: vol. 2: Issue. 1, Jan. 2009, Canada, 56 pages, http://dx.doi.org/10.1561/2200000006.
Jonnalagadda, Venkata Krishna, "Sparse, Stacked and Variational Autoencoder", Dec. 6, 2018, 15 pages, retrieved from https://medium.com/@venkatakrishna.jonnalagadda/sparse-stacked-and-variatinoal-autoencoder-efe5bfe73b64 (retrieved on May 4, 2020).
Lee, B-G., et al., "Real-time physiological and vision monitoring of vehicle driver for non-intrusive drowsiness detection", IET Communications, Nov. 25, 2011, vol. 5, Issue: 17, pp. 2461-2469.
Mazzillo, M., et al., "Silicon Photomultiplier Technology at STMicroelectronics", IEEE Transactions on Nuclear Science, vol. 56, No. 4, Sep. 2009, pp. 243-242.
Mazzillo, Massimo et al., "Electro-Optical Performances of p-on-n and n-on-p Silicon Photomultipliers", IEEE Trans. Electron Devices, vol. 59, No. 12, Dec. 2012, pp. 3419-3425.
Moller, Martin Fodslette, "A Scaled Conjugate Gradient Algorithm for Fast Supervised Learning", Neural Networks, Elsevier Science Publishers, Barking, GB, vol. 6, No. 4, Jan. 31, 1993, pp. 525-533.
Ryu, Gi-Seong et al., "Flexible and Printed PPG Sensors for Estimation of Drowsiness," IEEE Transactions on Electron Devices, vol. 65, No. 7, Jul. 2018, 8 pages.
Spachos, Petros et al., "Feasibility Study of Photoplethysmographic Signals for Biometric Identification", 17th International Conference on Digital Signal Processing (DSP), Greece, Jul. 2011, pp. 1-5.
Szankin, M., et al., "Long Distance Vital Signs Monitoring with Person Identification for Smart Home Solutions", 40th Annual International Conference of the IEEE Engineering in Medicine and Biology Society (EMBC), Jul. 2018, pp. 1558-1561.
Wan, Yongbo, et al., "Design of a Photoplethysmographic Sensor for Biometric Identification", International Conference on Control, Automation and Systems, Oct. 17-20, 2007, pp. 1897-1900.
Yao, Jianchu et al., "A Pilot Study on Using Derivatives of Photoplethysmographic Signals as a Biometric Identifier", 29th Annual International Conference of the IEEE Engineering in Medicine and Biology Society, Aug. 22-26, 2007, pp. 4576-4579.
Rundo, Francesco, et al., "An Advanced Bio-Inspired PhotoPlethysmoGraphy (PPG) and ECG Pattern Recognition System for Medical Assessment", Sensors, vol. 18, No. 2, Jan. 30, 2018, 22 pages.

\* cited by examiner

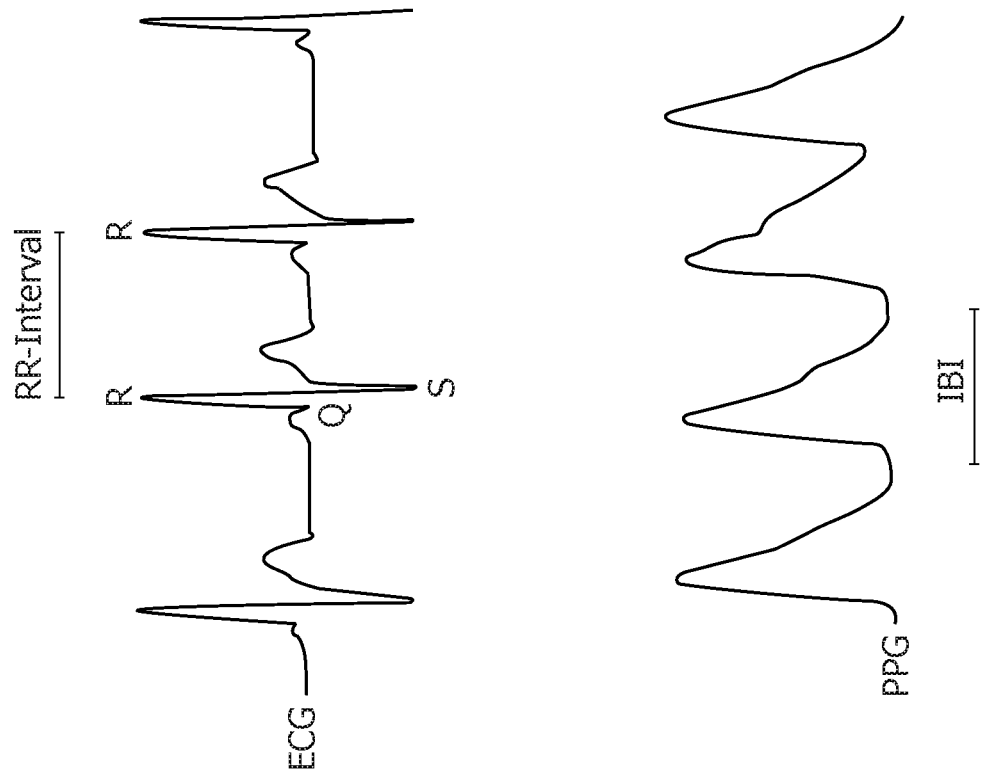

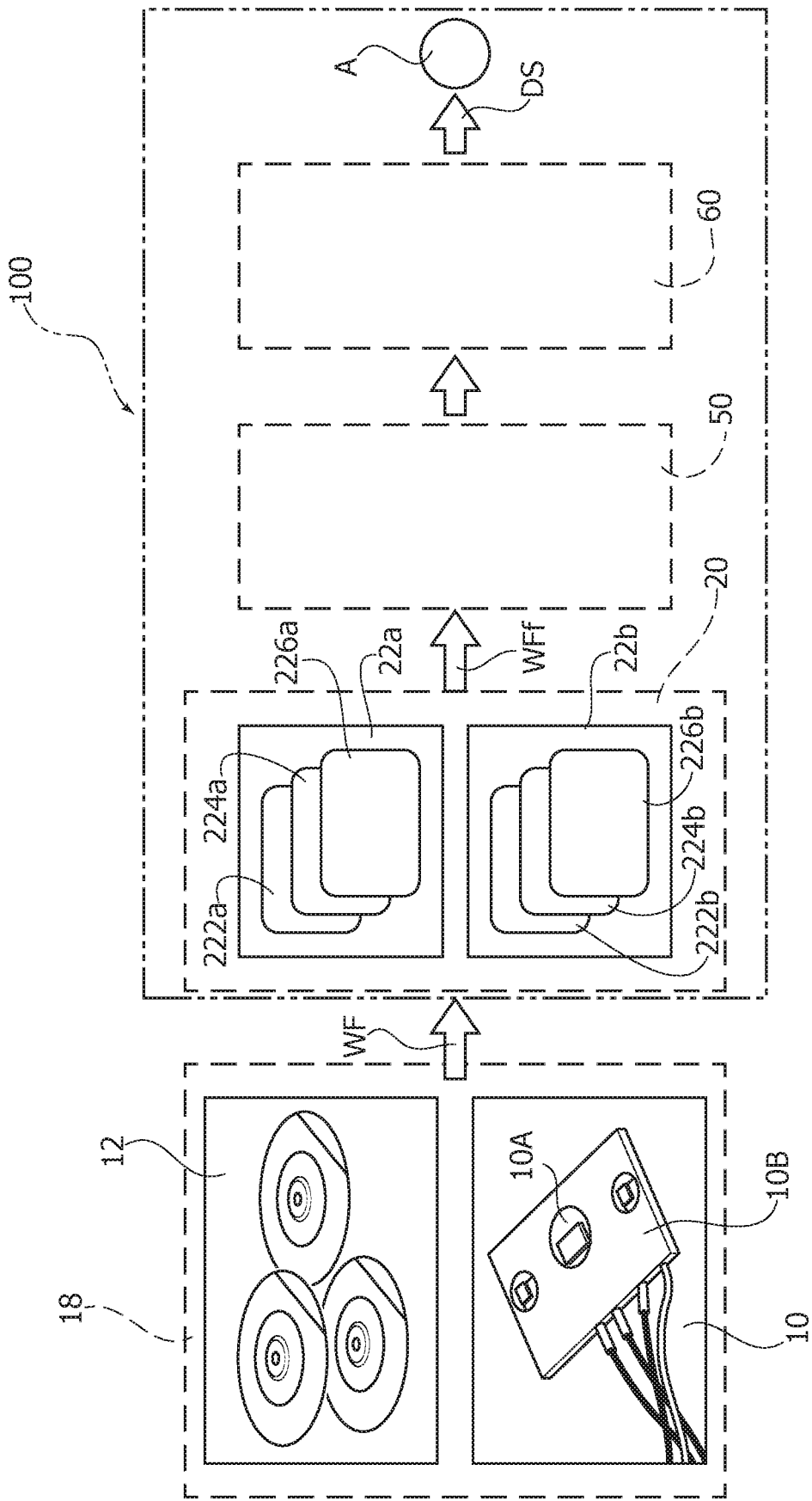

ELECTROPHYSIOLOGICAL SIGNAL PROCESSING METHOD, CORRESPONDING SYSTEM, COMPUTER PROGRAM PRODUCT AND VEHICLE

CROSS-REFERENCE TO RELATED APPLICATIONS

This application claims priority to Italian Patent Application No. 102019000005868, filed on Apr. 16, 2019, which application is hereby incorporated herein by reference.

TECHNICAL FIELD

The present invention relates generally to a system and method, and, in particular embodiments, to electrophysiological signal processing methods, corresponding systems, computer program products and vehicles.

BACKGROUND

Drowsiness of a vehicle driver (before and during driving) may adversely affect driving safety. Driver's drowsiness may cause serious road traffic accidents involving vehicles. The possibility to detect an attention state of a driver may facilitate evaluation of his/her fitness to drive a vehicle, facilitating to prevent road accidents.

It is known that a correlation exists between drowsiness and Heart Rate Variability (HRV), so that estimating HRV of e.g. a driver may permit to obtain useful information concerning possible drowsiness.

Heart rate variability (HRV) is the physiological phenomenon of variation in the time interval between heartbeats. Thus, HRV is indicative of autonomous nervous system activity state, which is responsible of operating automatic, unconscious and involuntary body activities, such as heartbeat activity.

An HRV value may be obtained via processing of measured electrophysiological signals related to heartbeats, e.g. ElectroCardioGraphy (ECG) and/or PhotoPletysmoGraphy (PPG) signals.

FIG. 1A is exemplary of a diagram of an ECG signal, while FIG. 1B is exemplary of a diagram of a PPG signal.

Using ECG, or electrocardiogram, it's typically the R peak that marks a heartbeat. Hence, the intervals between heartbeats are called R-R intervals, which may be used to compute HRV. Using PPG (PhotoPlethysmoGraphy), Inter-Beat Intervals, briefly IBIs, may be measured to compute HRV in place of R-R intervals.

For instance, if heartbeats in a measured ECG signal have a constant period, HRV may have a low value; conversely, HRV may have a high value in an opposite case.

For instance, if the ECG signal comprises an irregular pattern of heartbeats, it may indicate that the body is in a rest condition, while if the ECG signal comprises a regular pattern of heartbeats, it may be indicative of chronic stress in the body.

ECG signals may suffer from artifacts due to motion of micro-motion of a person during signal measurement.

PPG signals may have higher tolerance than ECG signals to such motion.

At least in principle, installing ECG detectors on the car steering wheel of a vehicle could be contemplated. Satisfactory operation would however require that (both) the driver's hands should be steadily placed on the car steering wheel at those positions where the ECG detectors are located. This is however a highly unrealistic scenario.

Moreover, as mentioned, HRV is linked to the attention state of the driver solely by a "second-order" correlation/dependency with drowsiness. HRV is linked to drowsiness due to the biological correlation between ECG and Autonomic Nervous System (ANS) activity (e.g., sympathetic, parasympathetic, enteric). ANS regulates key involuntary functions of the body, including heart activity.

Even in the (likely unrealistic) scenario of managing to detect an ECG signal on board the vehicle, or in the more realistic scenario of detecting a PPG signal on board the vehicle, generating alert signals and/or activating safety procedures based on HRV computed from those signals would still present some challenges, such as lengthy data buffering, for instance approximately 8 to 10 minutes of detected ECG time series would be used to provide a robust measure of driver drowsiness, leading to low-dynamic (e.g. slow) change-of-status/alert signaling, and complex frequency-domain signal processing involved in HRV computation, since HRV is linked to the frequency of detected ECG/PPG signals, would imply costly/slow CPU intensive computation.

Some authors propose to replace ECG/PPG with some EEG features, but even in this case frequency domain switching and CPU-intensive operations, as well as delay in drowsiness detection (data buffering), still represent a technological bottleneck.

Some authors propose to integrate a vision system to improve efficiency, which may come at the high price of increased costs and complexity.

As mentioned, an extensive activity is carried on and several approaches are proposed in literature as discussed below.

Jeyhani, Vala et al.: "Comparison of HRV parameters derived from photoplethysmography and electrocardiography signals", 2015, 37th Annual International Conference of the IEEE Engineering in Medicine and Biology Society (EMBC). 2015, pp. 5952-5955, discussing HRV analysis applied on beat-to-beat intervals obtained from ECG and PPG and discussing some important HRV parameters calculated from PPG-HRV and ECG-HRV, wherein maximum of PPG and its second derivative were considered as two methods for obtaining the beat-to-beat signals from PPG and the results were compared with those achieved from ECG-HRV.

M. Bolanos, et al.: "Comparison of Heart Rate Variability Signal Features Derived from Electrocardiography and Photoplethysmography in Healthy Individuals", 2006, International Conference of the IEEE Engineering in Medicine and Biology Society, New York, NY, 2006, pp. 4289-4294, discusses heart rate variability (HRV) signal used as a noninvasive marker in monitoring the physiological state of an individual and a PDA-based system developed to simultaneously record ECG and PPG signals to facilitate accurately controlled sampling and recording durations, wherein a comparison between different features of the HRV signals derived from both methods was performed to test the validity of using PPG signals in HRV analysis, using autoregressive (AR) modeling, Poincare' plots, cross correlation, standard deviation, arithmetic mean, skewness, kurtosis, and approximate entropy (ApEn) to derive and compare different measures from both ECG and PPG signals, providing potential support for the idea of using PPGs instead of ECGs in HRV signal derivation and analysis in ambulatory cardiac monitoring of healthy individuals.

Vicente, Jose et al.: "Detection of driver's drowsiness by means of HRV analysis", 2011, Computing in Cardiology (2011): p. 89-92, discusses driver's drowsiness detection based on biological and vehicle signals being studied in preventive car safety based on Autonomous Nervous System (ANS) activity which can be measured non-invasively from the Heart Rate Variability (HRV) signal obtained from surface ECG, presenting alterations during stress, extreme fatigue and drowsiness episodes in the hypothesis is that these alterations manifest on HRV, wherein an on-line detector of driver's drowsiness based on HRV analysis is developed, wherein two databases have been analyzed: one of driving simulation in which subjects were sleep deprived, and the other of real situation with no sleep deprivation.

G. Ryu et al., "Flexible and Printed PPG Sensors for Estimation of Drowsiness" in IEEE Transactions on Electron Devices, vol. 65, no. 7, pp. 2997-3004, July 2018, discusses printed flexible optoelectronic sensors composed of red organic light-emitting diodes (OLEDs) and organic photodiodes (OPDs) for detection of various biological signals in a photoplethysmogram (PPG) device, wherein PPG signals were successfully detected using the developed flexible PPG sensor and the conventional driving circuit, wherein subject drowsiness was estimated from heart rate variability, extracted from the PPG signals, using machine learning algorithms.

Sari, Nila Novita et al.: "A two-stage intelligent model to extract features from PPG for drowsiness detection", 2016, International Conference on System Science and Engineering (ICSSE) (2016), p. 1-2, discusses a two-stage intelligent model that combined the wavelet packet transform (WPT) and functional-link-based fuzzy neural network (FLFNN) to access drowsy level for early detection of drowsiness employing a sensor device that detects drowsy status at an early stage.

Kurian, Deepu et al.: "Drowsiness Detection Using Photoplethysmography Signal", 2014, Fourth International Conference on Advances in Computing and Communications (2014), p. 73-76, discusses an approach to detect drowsiness by using photoplethysmography signals, easily acquirable with non-invasive techniques, wherein Autonomous Nervous System (ANS) activity can be measured non-invasively from the Pulse Rate Variability (PRV) signal obtained from photoplethysmography signal (PPG), that comprises alterations during, relaxation, extreme fatigue and drowsiness episodes, developing an on-line detector of drowsiness based on PRV analysis, wherein the databases have been collected with the aid of an external observer who decides upon each minute of the recordings as drowsy or awake, and constitutes our data base.

Lee, B.-G. et al.: "Real-time physiological and vision monitoring of vehicle driver for non-intrusive drowsiness detection", IET Communications 5, 2011, p. 2461-2469, discusses an approach to detect driver's drowsiness by applying two distinct methods in computer vision and image processing, wherein the objective is to combine both methods under one single profile instead of relied solely on a detection method to enhance the driver's drowsiness detection resolution, therefore a non-intrusive drowsy-monitoring system is developed to alert the driver if driver falls into low arousal state, wherein photoplethysmography (PPG) is analyzed for its changes in signals waveform from awake to drowsy state, meanwhile eyes pattern or motion in image processing is addressed to detect driver fatigue, wherein genetic algorithm with template-matching approach is designed to detect eye region and estimate the drowsiness in different metric standard based on eyes behavior, wherein PPG drowsy signals are integrated with eyes motion to derive the final probability model for delivering valid and reliable drowsiness detection system.

SUMMARY

In an embodiment, a method of processing an electrophysiological signal includes collecting the electrophysiological signal that is indicative of a level of attention of a human; filtering the electrophysiological signal via joint low-pass and high-pass filtering using a set of filtering parameters including low-pass filters parameters and high-pass filters parameters having a set of low-pass cut-off frequencies and a set of high-pass cut-off frequencies respectively. The method further includes applying artificial neural network processing to the filtered electrophysiological signal to extract therefrom a set of features of the electrophysiological signal. The method further includes applying classifier processing to the set of features extracted from the filtered electrophysiological signal and producing a classification signal indicative of the level of attention of the human. The method further includes generating a trigger signal to trigger a user circuit based on the classification signal.

In an alternative embodiment, an electrophysiological signal processing system includes an electrophysiological signal sensor configured to collect an electrophysiological signal indicative of a level of attention of a human; a processor; a non-volatile memory including a program to be executed in the processor. The program includes instructions for: filtering the electrophysiological signal via joint low-pass and high-pass filtering using a set of filtering parameters including low-pass filters parameters and high-pass filters parameters having a set of low-pass cut-off frequencies and a set of high-pass cut-off frequencies respectively; applying artificial neural network processing to the filtered electrophysiological signal to extract therefrom a set of features of the electrophysiological signal; applying classifier processing to the set of features extracted from the filtered signal and producing a classification signal indicative of the level of attention of the human; and generating a trigger signal to trigger a user circuit based on the classification signal.

In an alternative embodiment, a vehicle includes an electrophysiological signal sensor configured to collect an electrophysiological signal indicative of a level of attention of a human; a processor; a non-volatile memory including a program to be executed in the processor, the program including instructions for: filtering the electrophysiological signal via joint low-pass and high-pass filtering using a set of filtering parameters including low-pass filters parameters and high-pass filters parameters having a set of low-pass cut-off frequencies and a set of high-pass cut-off frequencies respectively, applying artificial neural network processing to the filtered electrophysiological signal to extract therefrom a set of features of the electrophysiological signal, applying classifier processing to the set of features extracted from the filtered signal and producing a classification signal indicative of the level of attention of the human, and generating a trigger signal based on the classification signal; and a driver assistance device configured to be triggered by the trigger signal.

BRIEF DESCRIPTION OF THE DRAWINGS

One or more embodiments will now be described, by way of non-limiting example only, with reference to the annexed Figures, wherein:

FIGS. 1A and 1B are discussed in the foregoing;

FIG. 2A is a diagram exemplary of a processing pipeline for electrophysiological signals as per the present disclosure;

DETAILED DESCRIPTION OF ILLUSTRATIVE EMBODIMENTS

Figure 2B:
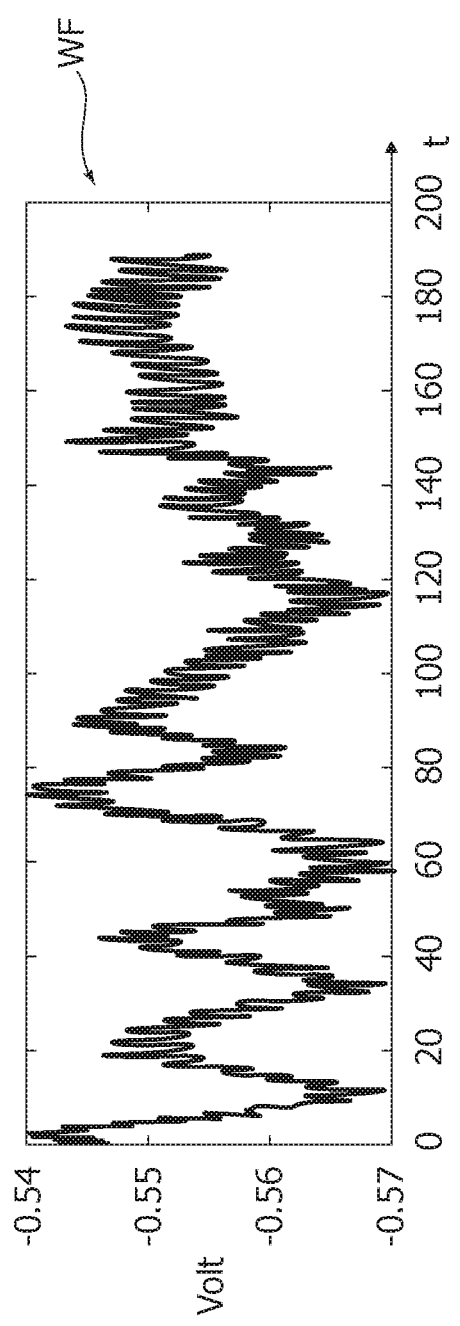
FIG. 2B is a diagram exemplary of possible time behavior of certain electrophysiological signals in embodiments.

The description relates to a method for electrophysiological signal processing such as, for instance, PhotoPlethysmoGraphy (PPG) signals.

One or more embodiments may be useful in obtaining information from a driver of a vehicle with a view to possibly generating alert signals and/or activating safety procedures (e.g. taking over control of the vehicle), for instance within the framework of an Advanced Driver-Assistance System (ADAS) or a Driver Alcohol Detection System for Safety (DADSS).

As mentioned, various solutions proposed in the literature may be exposed to one or more of the following drawbacks. Being based on HRV, existing methods employ ECG (not applicable in Automotive) or post-processed PPG. Lengthy data buffering, e.g. of 8/10 minutes of data, makes it difficult to perform efficient and robust continuous driver monitoring. Low dynamic (e.g., slow) change-of-status signaling (e.g. between drowsy/wakeful). Frequency Domain Analysis has to be employed, for instance Fast Fourier Transform (FFT) or Power Spectral Density (PSD). Methods relying solely on PPG signal detection may provide lower accuracy, which may be mitigated by the employ of vision system data, while increasing complexity. The existing methods use of CPU-intensive algorithms and have low compatibility with existing devices.

Existing solutions hence suffer from low-speed detection of a change in the state of an attention level of, e.g., a driver of a vehicle, especially while employing relatively cheap and low complexity components.

Embodiments of the invention discussed herein overcome these and other problems. One or more embodiments contribute in providing such an improved solution. According to one or more embodiments, such improved solution can be achieved by means of a signal processing method having the features set forth in the claims that follow.

An advanced time-based method for efficient and robust Near-Real Time continuous detection of driver's level of attention, using a sampled PPG signal of the same driver, may be exemplary of such a method.

One or more embodiments may relate to a corresponding system. An advanced driver assistance system configured to perform the signal processing method as per the present disclosure may be exemplary of such a system.

One or more embodiments may facilitate providing time-continuous drowsiness monitoring for a vehicle driver on-board the vehicle, e.g. increasing road safety. One or more embodiments comprise advanced time-based efficient and robust near real-time detection of continuous driver's level of attention, by using sampled PPG signal of the same driver.

One or more embodiments may comprise PPG detectors performing sampling of PPG time series of a car-driver (e.g., from solely one hand placed on the car steering, hence advantageously employing a single detection point).

One or more embodiments thus facilitate obtaining information (data, physical quantities) from the living human or animal body e.g. in support the diagnostic activity of a human in medical and veterinary activities or for other possible uses. Obtaining information on the behavior and/or the reaction of drivers and passengers in the automotive field is exemplary of one such possible use.

One or more embodiments may comprise a vehicle equipped with such PPG detectors and with such ADAS system configured to process signals detected by the PPG detectors.

One or more embodiments may facilitate continuous driver drowsiness detection/monitoring without the employ of frequency domain computations as well as without lengthy data-buffering.

One or more embodiments may comprise an ad-hoc (hyper)-filtering pipeline facilitating to extract, e.g. concurrently, various PPG signal features/dynamics.

One or more embodiments may adopt a processing pipeline including an electrophysiological raw signal adaptive filtering stage, including a pass-band scheme (e.g. low-pass plus high-pass), a pattern recognition system as well as a system for detecting and extract medical indicators.

One or more embodiments may comprise an ad-hoc high-speed machine learning pipeline configured to process such electrophysiological signal features/dynamics from filtering, facilitating to provide drowsy/wakeful classification of driver's state.

One or more embodiments may advantageously provide results quickly, e.g. employing between less than 8 seconds of PPG sampled signal and 1 minute for neural network training, even in the absence of a Graphical Processing Unit (GPU). In one or more embodiments, feed-forward pipeline may facilitate reducing the time employed up to 4/5 seconds.

In one or more embodiments, one-shot high-speed calibration may advantageously be employed, further reducing processing time.

One or more embodiments may use solely electrophysiological signal, e.g. PPG signal, samples for providing drowsiness detection with approximately 96% of accuracy, advantageously eliminating the presence of multiple signal types detection systems (e.g., Vision).

In one or more embodiments, CPU-intensive computations may be advantageously avoided, eliminating the use of frequency domain operations.

In one or more embodiments, high speed re-learning (if selected) may be advantageously be facilitated due to the adoption of a Scaled Gradient Conjugate neural network training method.

In the ensuing description, one or more specific details are illustrated, aimed at providing an in-depth understanding of examples of embodiments of this description. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in one or more points of the present description do not necessarily refer to one and the same embodiment.

Moreover, particular conformations, structures, or characteristics may be combined in any adequate way in one or more embodiments.

The references used herein are provided merely for convenience and hence do not define the extent of protection or the scope of the embodiments.

The drawings are in simplified form and are not to precise scale. For the sake of simplicity, directional (up/down, etc.) or motional (forward/back, etc.) terms may be used with respect to the drawings. The term "couple" and similar terms do not necessarily denote direct and immediate connections, but also include connections through intermediate elements or devices.

For the sake of simplicity, principles underlying the invention are discussed in the following mainly in relation to the processing of a PhotoPletysmoGraphy (PPG) signal. Such an electrophysiological signal type is purely exemplary, being otherwise understood that other types of electrophysiological signals may be processed in one or more embodiments, e.g. ElectroCardioGram (ECG) signals, ElectroEncephaloGram (EEG) signals, etc.

In one or more embodiments, a PPG signal may be simpler to employ as electrophysiological to process according to a method as disclosed herein, as it may be easier to sample in an automotive environment with respect to an ECG signal, due to a reduced invasiveness of the hardware in the limited volume of a vehicle.

As exemplified in FIG. 2A, one or more embodiments of a system for electrophysiological signal processing 100 may comprise an electrophysiological signal processing pipeline, comprising a collection stage 18, configured to collect at least one electrophysiological signal WF, e.g. a "raw" PPG/ECG signal WF as exemplified in FIG. 2B. The electrophysiological signal processing 100 includes a (hyper) filtering stage 20, configured to receive the electrophysiological signal WF received and apply filtering to it, preferably passband filtering via joint concurrent high pass filter 22a and low pass filter 22b, providing a set of filtered electrophysiological signals WFf, e.g. filtered PPG signals. For instance, the set of filtered signals WFf may be stored in a properly defined matrix having a number of columns equal to the number of filters $N_\omega$ employed in the filtering stage 20 and a number of rows equal to the number of PPG signals processed NPPG. The electrophysiological signal processing 100 further includes a pattern recognition processing stage 50, e.g. a first Artificial Neural Network (ANN) stage, configured to receive the set of filtered electrophysiological signals WFf and to apply pattern recognition 50 to it in order to detect an attention level of the driver. The electrophysiological signal processing 100 further includes a classifier stage, e.g. a second ANN processing stage 60, configured to classify an attention level of the driver, generating a signal indicative of the attention level of the driver, e.g. a driver drowsiness indicator, and providing it to user circuits A.

In one or more embodiments, the collection stage 18 may comprise PPG probe circuitry 10 can include a PPG probe section 10A and a printed circuit board (PCB) 10B configured for interfacing the probe sections 10A with an acquisition and processing circuit 18.

In one or more embodiments, the printed circuit board (PCB) 10B can be designed and used to interface the PPG probe(s) and an NI (National Instrument) acquisition instrumentation during the measurement of the PPG signals. Such an acquisition and processing circuit 18 as exemplified herein may also comprise a hardware/software platform based e.g. on a personal computer (e.g. with Intel core i5 3.4 GHz plus MATLAB) configured to acquire and process electrophysiological signals.

In the exemplary arrangement shown, the PPG probe section 10A can be coupled to the interface PCB 10B e.g. via USB cables with the interface PCB 10B in turn coupled with acquisition instrumentation 18, e.g. via SubMiniature version A (SMA) cables. Other arrangements known in the art for these purposes may of course be adopted for the connections.

In one or more embodiments, the probe section 10A can include SiPMs having associated, in a manner known per se, various ancillary components such as bandpass filters, LEDs, sensing resistors, bias capacitances.

In one or more embodiments the PPG probe section 10A can be based on the use of large area n-on-p SiPMs fabricated at STMicroelectronics (see, e.g., M. Mazzillo, et al.: "Silicon Photomultiplier technology at STMicroelectronics", IEEE Trans. Nucl. Sci, vol. 56, no. 4, pp. 2434-2442, 2009).

In one or more embodiments, the electrophysiological signal WF may be an ECG signal acquired via respective probes 12, which may be of conventional type.

As mentioned, in one or more embodiments, the "raw" electrophysiological signal data WF can also be collected "online" via ADAS systems, in view of processing in a processing circuit 100.

The results produced by the system 100 can possibly be presented on a display unit to an operator, e.g. a medical practitioner, with the capability of supporting his activity, e.g. for diagnostic purposes.

As repeatedly noted in the foregoing, PPG processing apparatus as discussed herein lends itself to be used in areas other than the medical field, e.g. in the automotive field in order to gain useful information on the behavior and/or the reaction of drivers and passengers in various situations which may occur in a motor vehicle.

FIG. 2B is a diagram exemplary of the PPG detected waveform (raw data) which can be obtained with a PPG signal detection device 18 including LEDs with specific wavelengths (usually infrared at 940 nm) and a SiPM photomultiplier of the type disclosed e.g. in the articles by M. Mazzillo, et al. already cited.

In such a device, light emitted by the LEDs is absorbed by the skin (DC component) and by the arteries, e.g. by oxygenated (and in small part by non-oxygenated) hemoglobin (AC component). Therefore, the residual reflected light (as resulting e.g. from back-scattering) will be proportional-differential with respect to the amount of light absorbed by the hemoglobin in the patient's blood in the various phases of the heart (systolic, diastolic, dicrotic, and so on). The (e.g. SiPM photomultiplier) PPG sensor will thus detect the presence of back-scattered photons (reflected light) by producing a corresponding electrical signal that can be sampled e.g. by 24-bit ADC (e.g. in the interface 10B of FIG. 2A) thus providing a PPG signal as shown in FIG. 2B.

For instance, document US Patent Publication 2019/0021615 A1 by the same Applicant discusses such a PPG sensor 10.

Such a signal includes the DC and the AC components, as well as various types on measurement noise, e.g. electronic noise, noise due to power supply (e.g. 50 Hz), noise due to movement of the patient's body, respiratory activity, and so on.

For most applications only the AC component of the PPG signal is helpful, the AC component lying e.g. in the 0.5-7.0 Hz frequency range. One or more embodiments as exemplified may thus include a filtering system (e.g. 20 in FIG. 2A) active in that range. Further frequency sub-bands of such range may be of interest to analyze, in order to extract more accurate indicators of attention level from the electrophysiological signal WF. In order to tackle such other frequency sub-bands and to combine information therein as discussed in the foregoing, one or more embodiments may include a (hyper) filtering stage (e.g. 20 in FIG. 2A), applying multiple filtering in various frequency ranges.

In one or more embodiments, the filtering stage 20 may be implemented in a processing circuit of a SPC 58 Chorus microcontroller unit (MCU) fabricated at STMicroelectronics.

As exemplified in FIG. 2A, (hyper) filtering 20 may comprise bandpass filtering via joint low-pass filter 22a and high-pass filter 22b.

Inventors have observed that employing such a hyperspectral approach may facilitate obtaining different representation of the information contained into original electrophysiological signal.

In one or more embodiments, a low-pass filter 22a and a high-pass filter 22b may comprise multiple filtering stages 222a, 224a, 226a, 222b, 224b, 226b. For instance, a low-pass filter 22a may comprise a first set of filters 222a, 224a, 226a having a first set of filter parameters, e.g. cut-off frequencies, filter types, etc., for instance within the PPG AC component frequency range 0.5-7.0 Hz. The high-pass filter 22b may comprise a second set of filters 222b, 224b, 226b having a second set of parameters, e.g. cut-off frequencies, filter types, etc. for instance within the PPG AC component frequency range 0.5-7.0 Hz.

In one or more embodiments, a same number of filter stages Nf may be present in the low-pass filter 22a and high-pass filter 22b.

In one or more embodiments, applying multiple bandpass filtering 20 to an electro-physiological signal WF may facilitate obtaining different representation of information contained into original signal. Filtering with different filter types and filter parameters may facilitate obtaining multiple features of a signal at a same time, reducing the speed of processing the signal to recognize a state of attention of the driver.

Figure 4:
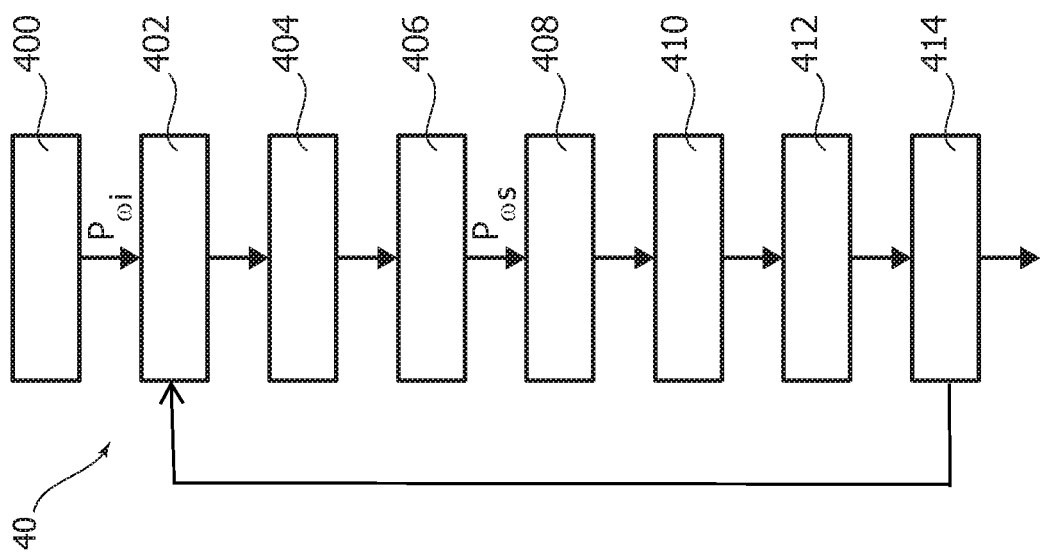
FIGS. 4, 5, 6A, and 6B are diagrams exemplary of principles underlying a processing pipeline for electrophysiological signals as per the present disclosure.

In one or more embodiments, the filtering stage parameters may be calibrated in a calibrating stage 40, comprising varying low-pass filter parameters 222a, 224a, 226a and high-pass filter parameters 222b, 224b, 226b in the set of filtering parameters, so that features extracted vary as a function of the variation of said low-pass filter parameters 222a, 224a, 226a and said high-pass filter parameters 222b, 224b, 226b, and selecting calibrated low-pass filter parameters 222a, 224a, 226a and high-pass filter parameters 222b, 224b, 226b that provide a fit of features extracted with respect to a reference set of features extracted and/or a reference classification signal, as further detailed in the following (see, e.g., FIG. 4).

Figure 3A:
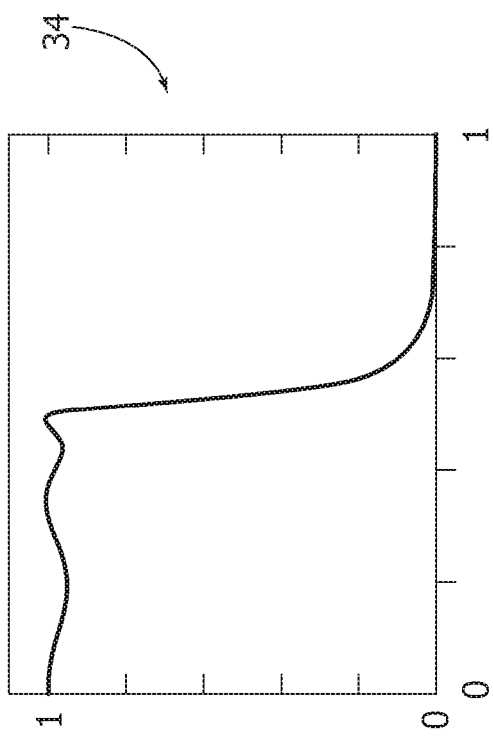
FIGS. 3A to 3E are diagrams exemplary of filtering parameter types.
Figure 3B:
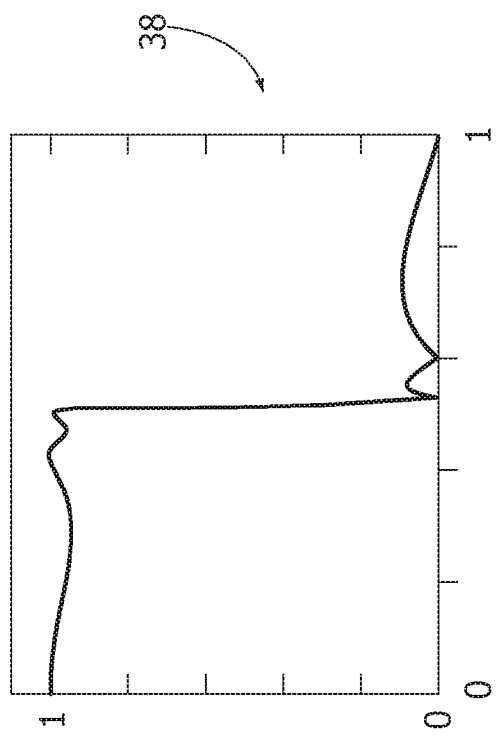
Figure 3C:
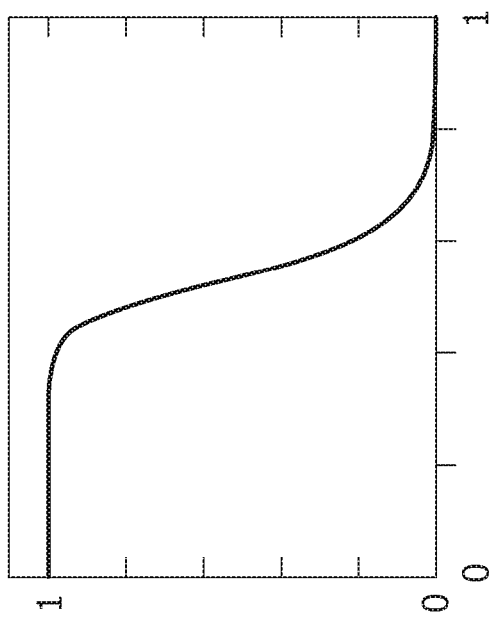
Figure 3D:
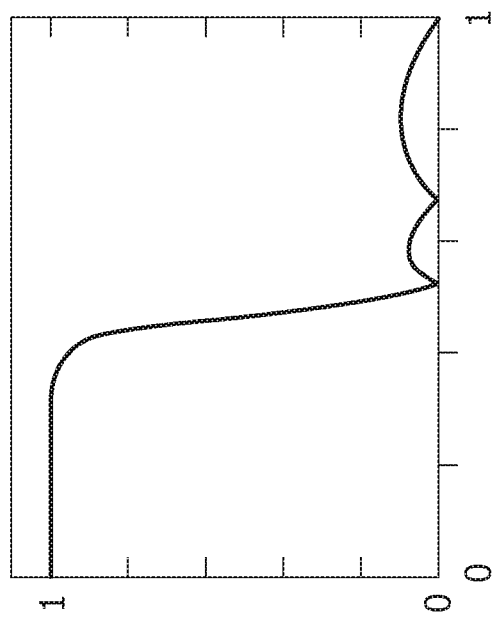

In one or more embodiments, one or more filter types may be found suitable for use in the filtering stage 20. For instance, suitable filters may have various transfer functions in frequency as exemplified in FIGS. 3A-3D, wherein: a Butterworth type may have a first transfer function 32 as exemplified in FIG. 3A, a Chebyshev type I type may have a second transfer function 34 as exemplified in FIG. 3B, a Chebyshev type II type may have a third transfer function 36 as exemplified in FIG. 3C, and an elliptic type transfer function may have a fourth transfer function 38 as exemplified in FIG. 3D.

Figure 3E:
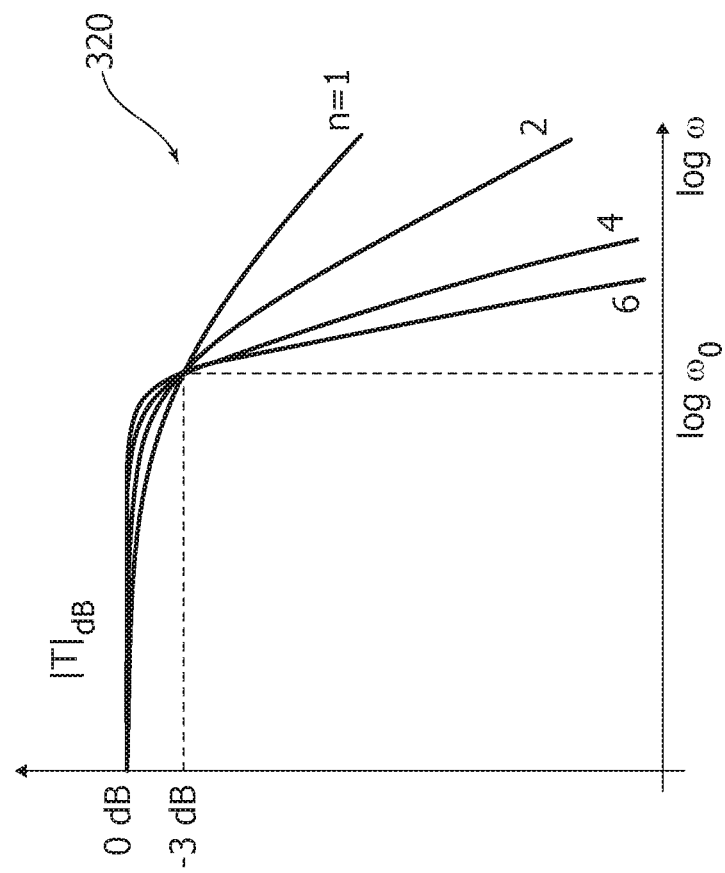

FIG. 3E is exemplary of a set of Butterworth filter transfer functions 320 Bode plot which may have a same cut-off frequency $\omega o$. The Butterworth filter is a type of signal processing filter designed to have a frequency response as flat as possible in the passband. For instance, the transfer function may be more or less close to an ideal descending step as a function of a parameter n having a high (e.g. n=6) or low (e.g. n=1) value, where n may be the number of poles of the filter transfer function in frequency.

One or more filter parameters (e.g., cut-off frequency, number of poles, etc.) of filters of a given type, e.g. Butterworth filters, chosen for use in the set of filter stages 22a, 22b, respectively, may be calibrated via an ad-hoc Genetic Algorithm Optimization Procedure (briefly, GAOP) 40. In one or more embodiments, such a GAOP 40 may be employed in finding optimal parameters, e.g. cut-off frequencies $\omega c$, for each filter in the (hyper) filtering stage, for instance for the filter 222a in the first set of filters 22a.

A Genetic Algorithm (briefly, GA) is a type of Evolutionary Algorithm (briefly, EA) that simulates the process of natural selection to find good if not optimal solutions to very complex problems. In EA, a set of potential solutions encoded as chromosomes are evaluated and scored via a fitness function. Based on the fitness score, better chromosomes are selected to generate the next generation of solutions or "off-spring." EA methods can be classified according to the means of offspring generation: GA, allows sexual reproduction (crossover operation) for offspring generation as well as mutations, as discussed in the following.

As mentioned, the evolution usually starts from a population of randomly generated individuals, and is an iterative process, with the population in each iteration called a generation. In each generation, the fitness of every individual in the population is evaluated; the fitness is usually the value of the objective function in the optimization problem being solved. The more fit individuals are stochastically selected from the current population, and each individual's genome is modified (recombined and possibly randomly mutated) to form a new generation. The new generation of candidate solutions is then used in the next iteration of the algorithm. Commonly, the algorithm terminates when either a maximum number of generations has been produced, or a satisfactory fitness level has been reached for the population.

A Self-Organizing map may also be found suitable for use in combination with the GA, as discussed in the following.

In one or more embodiments as exemplified in FIG. 4, the Genetic Algorithm Optimization Procedure (GAOP) 40 may comprise a population initialization stage 400, where a "population" set of Butterworth filters P$\omega$i having each a set of "genes" comprising a set of filter parameters, e.g. cut-off frequency, number of poles, have the genes values initialized to a set of random values, e.g. 11 different cut-off frequency values and number of poles values randomly drawn independently from two normal distributions, is generated for the chosen filter type for the filter 222a, e.g. a Butterworth filter having a n=4 poles. The GAOP 40 further includes a filtering test stage 402, in which the electrophysiological signal WF is filtered once by any filter in the population of Butterworth filters P$\omega$i generated in the population initialization stage 400, providing a population set of candidate electrophysiological signal features. The GAOP 40 further includes a clustering stage 404, e.g. comprising a Self-Organizing Map (SOM) artificial neural network processing stage, wherein clustering is applied to the set of filtered signals by the candidate population set of filters generated in the filtering test stage 402.

The GAOP 40 further includes a fitness computation stage 406, in which a fitness function is computed for any of the Butterworth filters in the population of Butterworth filters Pωi using values generated in previous steps; for instance, when applied to a PPG signal, the fitness function employed in stage 406 of the GAOP 40 may be defined as:

$$f = \Sigma_k \tfrac{1}{2}(f(ppg_k) - SOM_j(ppg_k))^2$$

Such an expression may be indicative of a selection of the fitness function in stage 406 of the GAOP 40 as a function of a quadratic difference between a cluster (centroid) of filtered waveforms of the electrophysiological signal, e.g. a first electrophysiological signal of a wakeful human and a second electrophysiological signal of a drowsy human as discussed in the following, and the weights of neurons of the SOM belonging to its neighborhood. Such a fitness function expression may facilitate reaching a stationary condition in which a single significant cluster (weight) $f\,(ppg_k)$ together with neighboring weights of the SOM $SOM_j(ppg_k)$ "survive" for each electrophysiological signal type filtered.

In one or more embodiments, the GAOP 40 may facilitate optimizing such a fitness function, e.g. finding a set of cut-off frequencies that maximizes such a quadratic difference, as a result of reducing SOM weight values with respect to a dominating value of the single weight value that may represent the cluster wherein the filtered electrophysiological signals lie.

The GAOP 40 further includes a selection stage 408, in which random filters in the population of filters Pωi are selected and other are discarded via a "roulette wheel" method based on weighted fitness functions values computed at stage 406. The selected filters make up a "parent" population of Butterworth filters Pωs.

The GAOP 40 further includes a reproduction stage 410, where a new generation of "off-spring" filters Pωsc is generated by crossing-over genes from each couple of parent filters in the population of parent filters Pωs, for instance generating a child filter having a cut-off frequency value equal to the one of a first parent filter and a number of nodes equal to the one of a second parent filter, different from the first parent filter.

The GAOP 40 further includes a mutation stage 412, in which occasionally one gene of the new generation of off-spring filters Pωs is varied from the value assigned at the previous step to a random number.

The GAOP 40 further includes a new generation initialization stage 414, which is employed as a new "parent" generation in a subsequent iteration of stages 402 to 410.

This generational process is repeated until a "termination condition" has been reached. Common terminating conditions may be: minimum criteria satisfaction, fixed number of generations reached, the highest-ranking solution's fitness is reaching or has reached a plateau such that successive iterations no longer produce better results, manual inspection and/or combinations of the above.

Although crossover and mutation are known as the main genetic operators, it is possible to use other operators such as regrouping, colonization-extinction, or migration.

It may be worth tuning parameters such as the mutation probability, crossover probability and population size to find reasonable settings for the problem class being worked on.

Figure 5:
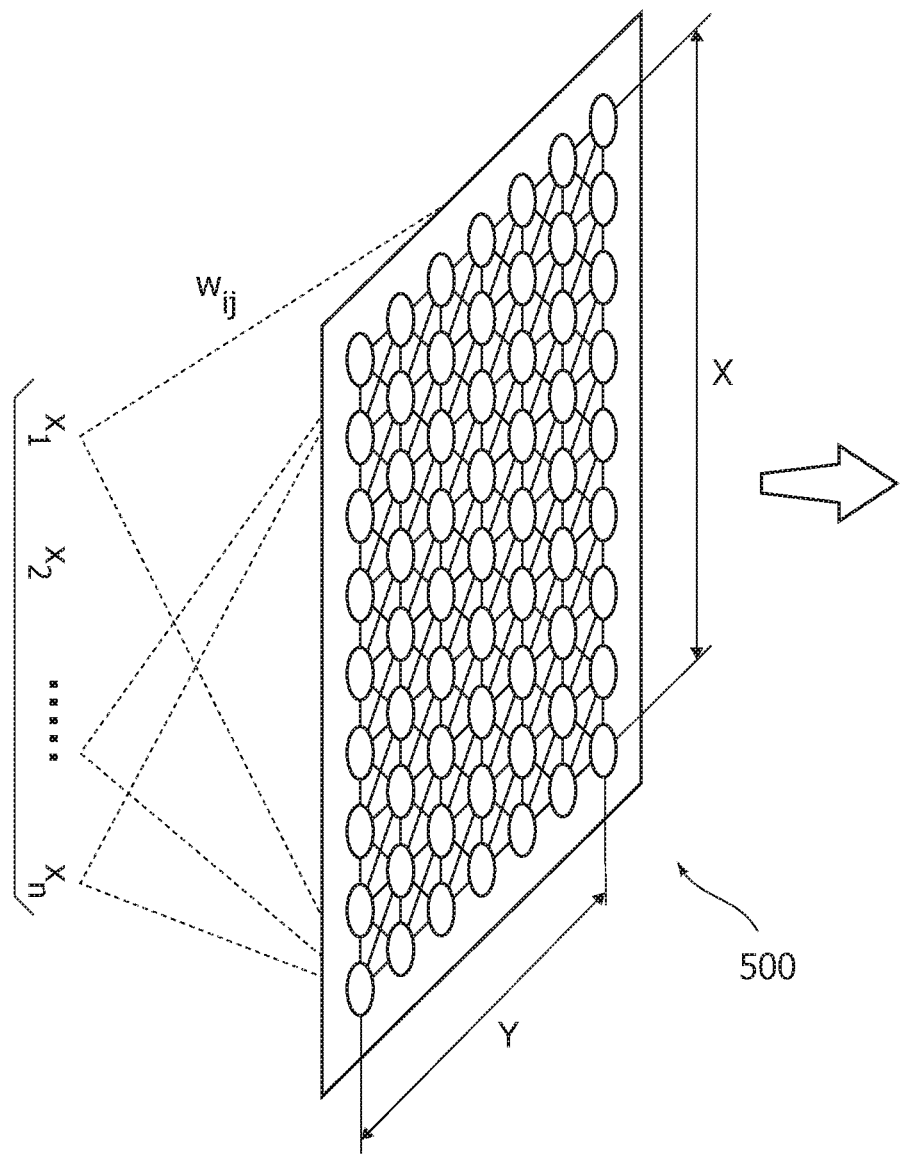

An extended SOM (Self Organizing Map) as schematically exemplified in FIG. 5 (where only the output layer 500 is visible) is found to be suited for use in one or more embodiments.

A self-organizing map (SOM) approach such as e.g. "Winner-Take-All" will activate the neuron that minimizes a distance (based on certain metrics, e.g. Euclidean) between its synaptic weights (w(t)) and the feature pattern.

The activated (distance-minimizing) neuron will therefore activate the neurons in its neighborhood (defined e.g. by a classical Gaussian function $\beta(x,y,t)$ and the output layer of the neural network, that is, a corresponding output neuron and its relative neighborhood (again defined by $\beta(x,y,t)$). The activated neuron is "rewarded" with becoming more like the fed data. The closer a node is to the so-called Best Matching Unit, BMU, network, the more its weights $w_o$ get altered while the farther away the neighbor is from the BMU the less its weight values vary.

For instance, in one or more embodiments, the SOM may comprise an input neural layer (e.g. lattice-like, for instance $n*n=n2$ neuronal nodes), which may receive as input the set of filtered signals WFf and a corresponding output layer 500 (e.g. lattice-like, for instance $n*n=n^2$ neuronal nodes), which may provide at output the vector of selected weights U.

In one or more embodiments, a random element $\mu(t)$ may be comprised with a view to improving the learning process.

In fact, from an initial distribution of random weights, and over many iterations, the SOM may be trained to facilitate providing at output a feature map of the input. The feature map may be provided at output in the form of a vector of selected weights U comprising a plurality of weight values. The plurality of values may be the result of the selection at the output layer 500 of the SOM of a plurality of parameters of best matching units (BMUs) neurons.

In one or more embodiments, the SOM used for the clustering stage 404 may be trained, e.g. its weights wij, $u_{ij}$ may be determined, through an iterative process based on providing a training set of electrophysiological signals stored in a memory in the processing circuit.

Specifically, in one or more embodiments the Self-Organizing Map (SOM) artificial neural network processing stage the clustering stage 404 may facilitate verifying whether a distribution of filter parameters, e.g. cut-off frequencies, may have a certain distribution which may be employed as "termination condition" for the GAOP 40, e.g. employing a heuristic approach.

For instance, such an operation of verifying the distribution of filter parameters may use the SOM to cluster a first filtered electrophysiological signal, collected from the human in a wakeful state, and a second filtered electrophysiological signal, collected from the human in a drowsy state. In the example considered, if the SOM clusters such signals in two groups, the test filter parameters may be considered as those of interest and the GAOP 40 may end. Conversely, in the example considered, if the clustering of the SOM leads to, e.g., identifying more than two groups, the GAOP 40 may progress towards another iteration.

In one or more embodiments, multiple iterations (e.g. a finite pre-defined number of iterations) of operations of the calibration GAOP 40 as exemplified herein may lead to determining that: in the first filter 22*a*, filters in the set of filters 222*a*, 224*a*, 226*a* may comprise a set of 11 filters having respective low-pass cut-off frequencies equal to: 0.5 Hz, 1.5 Hz, 2.2 Hz, 2.75 Hz, 3.12 Hz, 3.65 Hz, 4.1 Hz, 4.487 Hz, 5.23 Hz, 5.3 Hz, 6.11 Hz. In the second filter 22*b*, filters in the set of filters 222*b*, 224*b*, 226*b* may comprise a set of 11 filters having respective high-pass cut-off frequencies equal to: 1 Hz, 1.34 Hz, 2.09 Hz, 2.321 Hz, 3.09 Hz, 3.44 Hz, 4.2 Hz, 4.23 Hz, 5.2 Hz, 5.52 Hz, 6.87 Hz.

As mentioned, in one or more embodiments, determining or selecting filter parameters, e.g. cut-off frequencies $\omega_c$, of filtering stages 22*a*, 22*b* in the hyper-filtering stage 20 may employ the use of a genetic algorithm applied on a set of filtered electrophysiological signal WFf, e.g. obtained from a set of PPG signals which have been previously pre-processed via dedicated processing, to extract features therein and whose features may hence be somehow predetermined.

Such pre-processing may comprise, for instance, a "bio-inspired" PPG Pattern Recognition System—BI-P2RS—facilitating stabilization and denoising signal processing method. For instance, such a pre-processing method may employ Cellular Neural Networks adequately configured, for instance as disclosed in document US Patent Publication 2019/0021615 A.

The number filters in the first 222a and second 222b set of filters discussed herein is purely exemplary and in no way limiting, being otherwise understood that any number of filters may be employed.

The diagram of FIG. 5 shows how the block 404 may complete learning of a non-linear model which makes it possible to map the input filter parameters onto a corresponding electrophysiological signal feature pattern.

For instance, in one or more embodiments, the electrophysiological signals filtered in the preceding filter stage 402 can be input to the clustering stage 404 which may comprise an input neural structure (e.g. lattice-like, for instance 8×8=64 neurons).

Figure 6A:
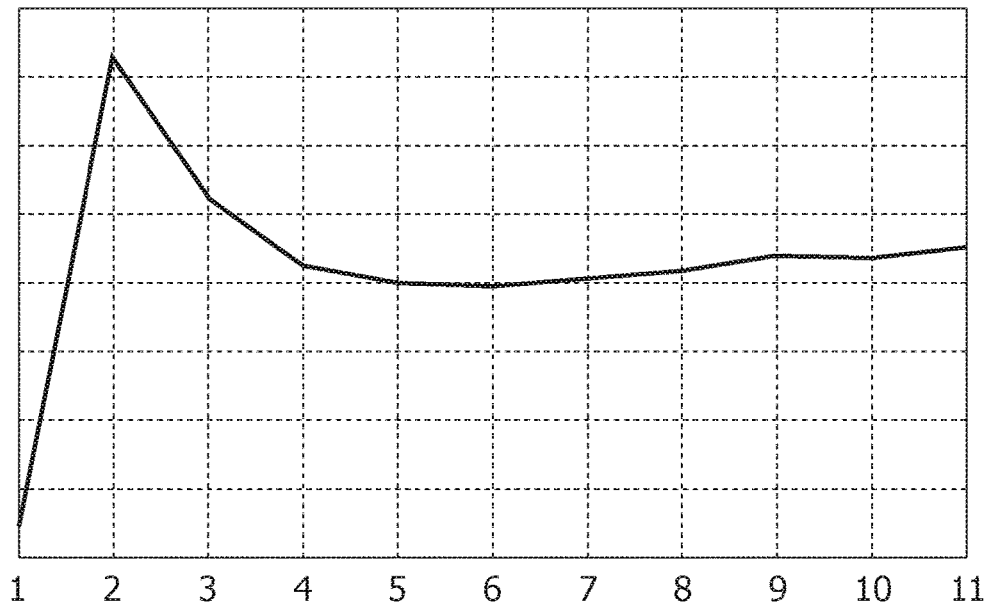
Figure 6B:
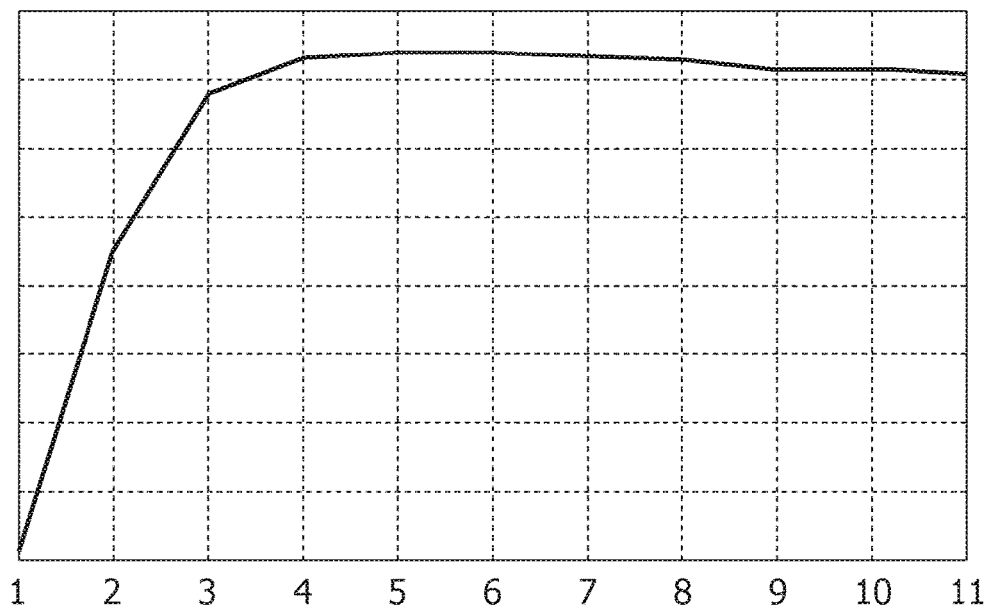

FIGS. 6A and 6B are exemplary of filtered electrophysiological signals WFf, e.g. PPG signals, provided as output by the hyper-filtering stage 20 employing eleven filters designed as discussed in the foregoing (e.g. method 400) applied to the PPG signal WF.

For instance, FIG. 6A is exemplary of a plot of values of filtered PPG signals for each k-th Low-Pass filter in the set of eleven low-pass filters, wherein the horizontal axis represents the k-th filter number and the vertical axis the value point of the PPG signal sample filtered by such k-th filter respective k-th low pass cut-off frequency. FIG. 6B is exemplary of a plot of values of filtered PPG signals for each k-th High-Pass filter in the set of eleven high-pass filters, wherein the horizontal axis represents the k-th filter number and the vertical axis the value point of the PPG signal sample filtered by such k-th filter respective k-th high pass cut-off frequency.

In one or more embodiments as exemplified in FIG. 2A, the set of filtered signals WFf may be processed in a pattern recognition processing 50.

Figure 7:
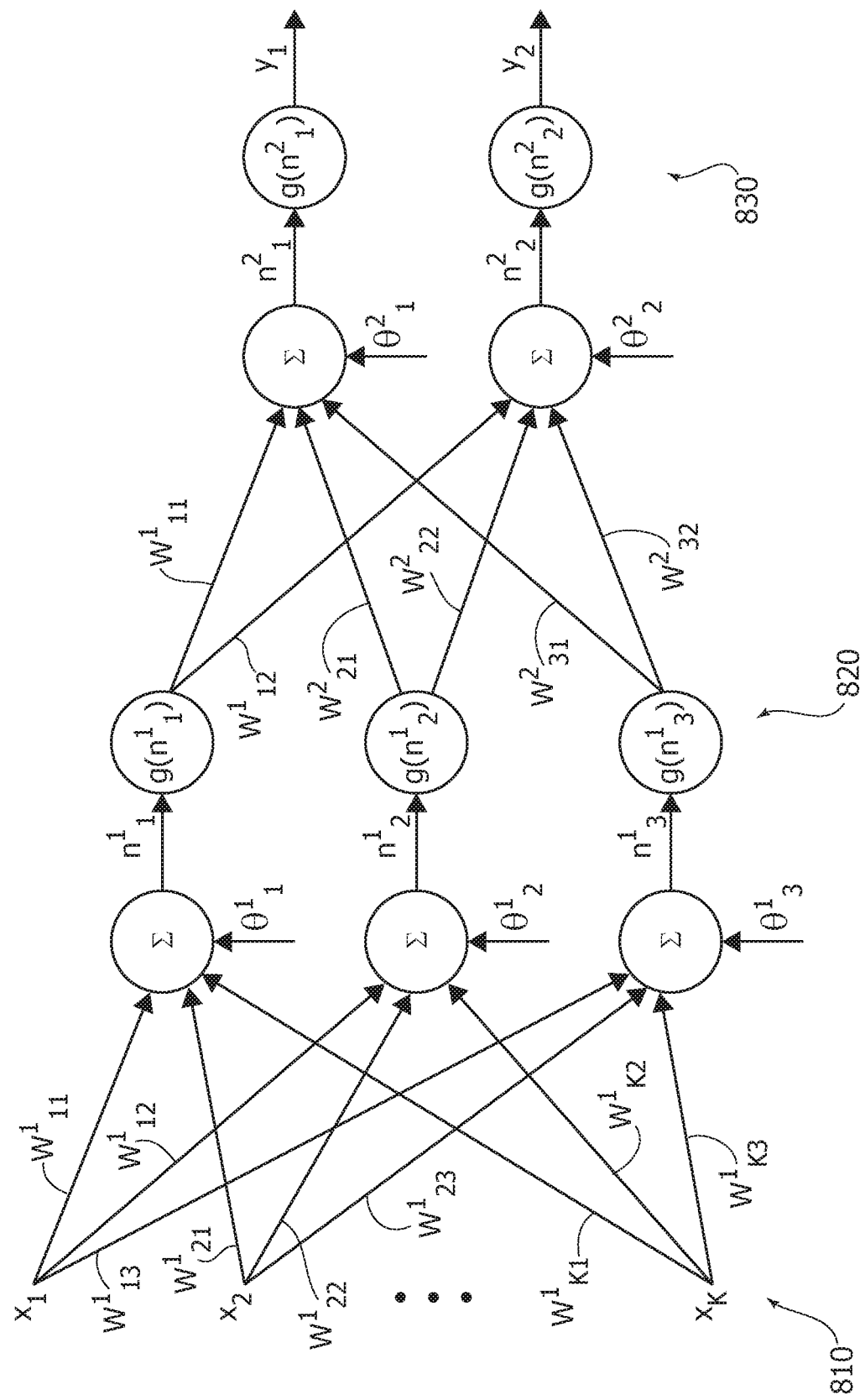
FIGS. 7 and 8 are diagram exemplary of portions of the diagram as exemplified in FIG. 2.

In one or more embodiments, a Scaled Gradient Conjugate Fully-Connected (briefly, SGC-FC) Regression method as exemplified in FIG. 7 may be found suitable for use in training the artificial neural network employed in the pattern recognition processing stage 50. For instance, such an artificial neural network 50 may be trained employing the method known from document M. Moller, "A Scaled Conjugate Gradient Algorithm for Fast Supervised Learning", Neural Networks, Vol. 6, pp. 525-533, '99, which discusses a supervised learning algorithm (Scaled Conjugate Gradient, SCG) with superlinear convergence rate.

The method is based upon a class of optimization techniques well known in numerical analysis as the Conjugate Gradient Methods. SCG uses second order information from the neural network but requires only O(N) memory usage, where N is the number of weights in the network. SCG may yield a speed-up of at least an order of magnitude depending on the convergence criterion, e.g., the bigger demand for reduction in error the bigger the speed-up. SCG is fully automated including no user dependent parameters and avoids a time-consuming line-search.

In one or more embodiments, a Scaled Conjugate Gradient (SCG) method denotes the quadratic approximation to the error E in a neighborhood of a point.

As exemplified in FIG. 7, such SGC-FC Regression layer 50 may comprise an input layer 810, comprising input nodes x1, x2, . . . , xK, for corresponding input values x1, x2, . . . , xK, at least one hidden layer 820, comprising hidden layer summation nodes Σ, providing respective weighted sums of input values with respective weights and hidden output nodes g(n11), g(n21), g(n31), and an output layer 830, comprising summation nodes E of values from previous layers with respective weights and output nodes y1, y2.

In one or more embodiments as exemplified in FIG. 2A, the set of filtered signals WFf may be processed in a classification processing stage 60.

Figure 8:
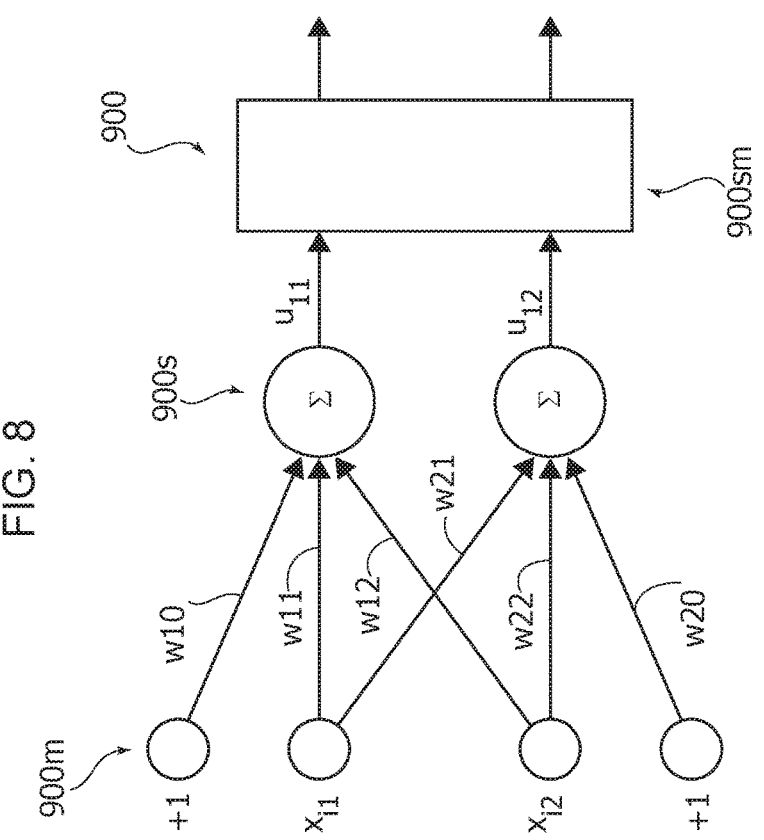

In one or more embodiments as exemplified in FIG. 8, a softmax layer 900 may be found suitable for use in the classification processing stage 60.

Softmax Regression layer is a generalization of logistic regression that may be found suitable for use for multi-class classification under the assumption that the classes are mutually exclusive: e.g., a level of attention of a driver may be classified either as drowsy either as wakeful.

In one or more embodiments, the softmax layer 900 comprises a set of neurons 900*m*, for instance m=4 neurons, configured to weight input data $x_{i1}$, $x_{i2}$ by respective weights $w_{11}$, $w_{12}$, $w_{12}$, $w_{22}$, $w_{20}$ and bias values +1. Weighted input data and bias values are then added therebetween in respective summation nodes 900*s* to provide a set of values $u_{11}$, $u_{12}$ onto which a softmax function is applied/computed. The softmax function may be represented as:

$$\Pi_{i1} = \frac{e^{x_i w_j}}{e^{x_i w_1} + e^{x_2 w_j}}$$

When applied to distinguish between two classes, as exemplified in FIG. 8, a softmax layer 900*sm* may compute respective softmax function values for each of the weighted input values for instance as:

$$\Pi_{i1} = \frac{e^{x_i w_j}}{e^{x_i w_1} + e^{x_2 w_j}} \text{ and }$$

$$\Pi_{i2} = \frac{e^{x_i w_j}}{e^{x_i w_2} + e^{x_2 w_2}} \text{ so that } \Pi_{i1} + \Pi_{i2} = 1$$

In one or more embodiments, the classification processing stage 60 may provide as output a signal DS, e.g. having a value between 0 and 1, which may be used to classify the state of the driver as either wakeful or drowsy, for instance as a function of a threshold first value. If the output stage signal DS has a value between the first value, e.g. 0.0, and a second value, e.g. 0.5, the driver attention state is classified as wakeful (class=0). If the output stage signal DS has a value between a third value, e.g. 0.51, and a fourth value, e.g. 1.0, the driver attention state is classified as drowsy (class=1).

One or more embodiments have been tested over electrophysiological signals, e.g. PPG signals, collected from seventy patients with different ages, sex, and so on, with at least five minutes of PPG sampling in respective drowsy/wakeful state under physiologists' directive (for instance together with ElectroEncephaloGram—EEG waves sampling).

One or more embodiments of the classification processing stage 60, as exemplified in FIG. 2A, may be configured to evaluate a state of the vehicle driver, for instance by providing a signal DS indicative of the level of attention of the driver D which may be fed to an interface A (for instance a display unit, a sound and/or light generator, and so on), in particular in case of detected drowsiness (e.g. when DS=1).

This may facilitate, for instance, making the driver aware of a reduced level of attention, possibly due to drowsiness or other reasons.

In one or more embodiments, processing the electrophysiological signal via artificial neural network processing 50 and classification processing 60 as discussed herein may be implemented in a processing circuit of an Accordo 5 processor fabricated at STMicroelectronics.

One or more embodiments may employ an optional parallel employing Convolutional Neural Network processing (CNN) for face expressions recognition together with an image processing system to make the system robust to unexpected errors, for instance facilitating high speed one-shot calibration via a time series of 4 seconds of recorded images of, e.g., an eye blink before and after the blink.

Figure 9:
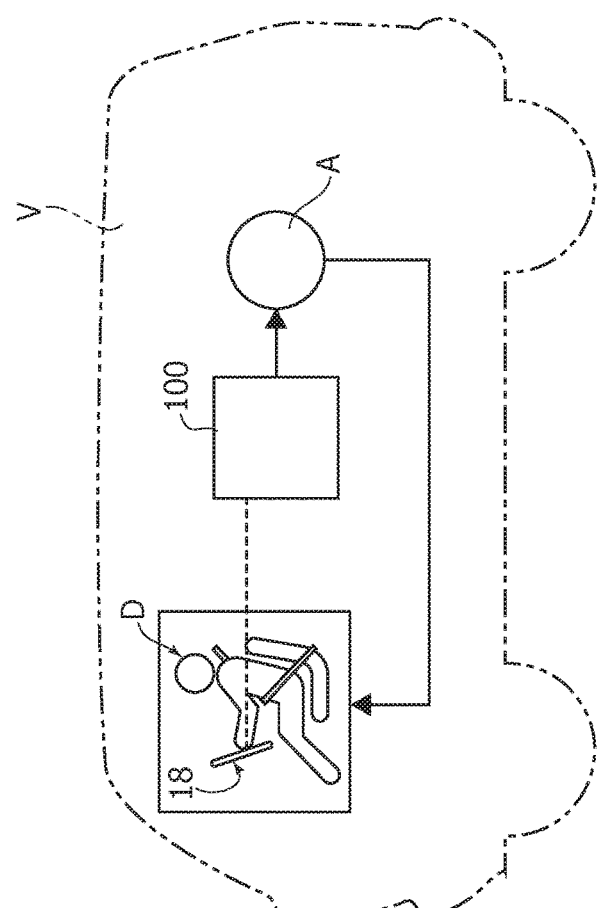
FIG. 9 is exemplary of a vehicle equipped with a system as per the present disclosure.

In one or more embodiments as exemplified in FIG. 9, a vehicle V may be equipped with the system 100 and the indicator of drowsiness DS of a driver D on board the vehicle V may be provided to further processing units and may be used to trigger an alert on an interface (see e.g. interface A) such as a display, e.g. on the dashboard of the vehicle V.

One or more embodiments comprise a method (for instance, 100) of processing at least one electrophysiological signal (for instance, WF) collected (for instance, 10, 12, 18) from a human (for instance, D), wherein the at least one electrophysiological signal collected is a function of the level of attention of said human. In one or more embodiments, the method may comprise filtering (for instance, 20) the at least one electrophysiological signal collected (for instance, WF) via joint low-pass (for instance, 22a) and high-pass (for instance, 22b) filtering using a set of filtering parameters (for instance, Pωs) including low-pass filters parameters (for instance, 222a, 224a, 226a) and high-pass filters parameters (for instance, 222b, 224b, 226b) having a set of low-pass cut-off frequencies and a set of high-pass cut-off frequencies, respectively.

The method may further comprise applying artificial neural network processing (for instance, so) to the at least one filtered electrophysiological signal (for instance, WFf) to extract therefrom a set of features of the at least one electrophysiological signal (for instance, WF) collected (for instance, 10, 12, 18). The method may further comprise applying classifier processing (for instance, 60) to the set of features extracted from the at least one filtered signal and producing a classification signal (for instance, DS) indicative of a level of attention of a human (for instance, D). The method may further comprise triggering a user circuit (for instance, A) as a function of said classification signal (for instance, DS).

In one or more embodiments, the electrophysiological signal may comprise a PPG signal (for instance, 10) or an ECG signal (for instance, 12).

In one or more embodiments, said set of filtering parameters may comprise low-pass and high-pass filters parameters selected from Butterworth, Chebyshev type I, Chebyshev type II and elliptic filter parameters.

One or more embodiments of the method may comprise comparing said classification signal (for instance, DS) with an attention threshold level, and triggering an alert circuit (for instance, A) as a result of said classification signal reaching said attention threshold level.

In one or more embodiments the at least one electrophysiological signal collected from the driver (for instance, D) of a vehicle (for instance, V) and the user circuit triggered as a function of said classification signal may comprise a user circuit (for instance, A) on board the vehicle.

In one or more embodiments, the at least one electrophysiological signal may be collected from the driver of a vehicle (for instance, V) via a PPG sensor (for instance, 10) or an ECG sensor (for instance, 12) on board the vehicle (for instance, V).

In one or more embodiments, applying artificial neural network processing (for instance, 50) may comprise applying Scaled Conjugate Gradient Fully Connected layer neural network processing.

In one or more embodiments, the method may comprise calibrating (for instance, 40) said set of filtering parameters (for instance, Pωs). In one or more embodiments, said calibrating may comprise varying low-pass filter parameters (for instance, 222a, 224a, 226a) and high-pass filter parameters (for instance, 222b, 224b, 226b) in said set of filtering parameters (for instance, Pωs), wherein said set of features extracted and/or said classification signal (for instance, DS) vary as a function of the variation of said low-pass filter parameters (for instance, 222a, 224a, 226a) and said high-pass filter parameters (for instance, 222b, 224b, 226b). The method may further comprise selecting calibrated low-pass filter parameters and high-pass filter parameters in said set of filtering parameters as low-pass filter parameters (for instance, 222a, 224a, 226a) and high-pass filter parameters (for instance, 222b, 224b, 226b) in said set of filtering parameters (for instance, Pωs) providing a fit (for instance, 406) of said set of features extracted and/or said classification signal (for instance, DS) with a reference set of features extracted and/or a reference classification signal.

In one or more embodiments, said calibrating mat comprise a genetic algorithm (for instance, 40) for selecting said calibrated low-pass filter parameters and high-pass filter parameters in the set of filtering parameters.

One or more embodiments may comprise an electrophysiological signal processing system, configured to be coupled to at least one electrophysiological signal sensor (for instance, 10, 12) collecting from a human (for instance, D) at least one electrophysiological signal (for instance, WF) which is a function of the level of attention of said human (for instance, D), wherein the system comprises processing circuitry configured to perform said acts of filtering (for instance, 20) of the electrophysiological signal collected (for instance, WF), applying said artificial neural network processing (for instance, 50) to the filtered electrophysiological signal (for instance, WFf), applying said classifier processing (for instance, 60) and triggering said user circuit (for instance, A) with one or more embodiments of the method (for instance, 100).

One or more embodiments may comprise a vehicle (for instance, V) equipped with one or more embodiments of the system in combination with at least one electrophysiological signal sensor, the system configured to collect from a human (for instance, D) at least one electrophysiological signal (for instance, WF) which is a function of the level of attention of said human (for instance, D).

In one or more embodiments, the vehicle may be equipped with at least one driver assistance device (for instance, A) configured to be triggered as a function of the classification signal.

One or more embodiments may comprise a computer program product loadable in the memory of at least one processing circuit and comprising software code portions for executing the steps of the method of any of claims 1 to 9 when the product is run on at least one processing circuit.

It will be otherwise understood that the various individual implementing options exemplified throughout the figures accompanying this description are not necessarily intended to be adopted in the same combinations exemplified in the figures. One or more embodiments may thus adopt these (otherwise non-mandatory) options individually and/or in different combinations with respect to the combination exemplified in the accompanying figures.

Without prejudice to the underlying principles, the details and embodiments may vary, even significantly, with respect to what has been described by way of example only, without departing from the extent of protection. The extent of protection is defined by the annexed claims.

The claims are an integral part of the technical teaching provided herein with reference to the embodiments.

What is claimed is:

1. A method of processing an electrophysiological signal, the method comprising:
   collecting the electrophysiological signal that is indicative of a level of attention of a human, the electrophysiological signal comprising a PhotoPletysmoGraphy (PPG) signal;
   filtering the electrophysiological signal via joint low-pass and high-pass filtering using a set of filtering parameters including low-pass filters parameters and high-pass filters parameters having a set of low-pass cut-off frequencies and a set of high-pass cut-off frequencies respectively;
   applying a first artificial neural network processing to the filtered electrophysiological signal to extract therefrom a set of features of the electrophysiological signal;
   applying a second artificial neural network processing to the set of features extracted from the filtered electrophysiological signal to produce a classification signal indicative of the level of attention of the human; and
   generating a trigger signal to trigger a user circuit based on the classification signal.

2. The method of claim 1, wherein the electrophysiological signal further comprises an ElectroCardioGraphy (ECG) signal.

3. The method of claim 1, wherein the set of filtering parameters comprises low-pass and high-pass filters parameters selected from Butterworth, Chebyshev type I, Chebyshev type II and elliptic filter parameters.

4. The method of claim 1, further comprising:
   comparing the classification signal with an attention threshold level, wherein when the classification signal reaches the attention threshold level, the trigger signal is configured to trigger an alert circuit.

5. The method of claim 1, wherein the electrophysiological signal is collected from a driver of a vehicle and the user circuit comprises a user circuit on board the vehicle.

6. The method of claim 5, wherein the electrophysiological signal is collected from the driver of the vehicle via a PhotoPletysmoGraphy (PPG) sensor or an ElectroCardioGraphy (ECG) sensor on board the vehicle.

7. The method of claim 1, wherein applying artificial neural network processing comprises applying Scaled Conjugate Gradient Fully Connected layer neural network processing.

8. The method of claim 1, further comprises calibrating the set of filtering parameters, wherein the calibrating comprises:
   varying low-pass filter parameters and high-pass filter parameters in the set of filtering parameters, wherein the set of features extracted and/or the classification signal (DS) vary as a function of a variation of the low-pass filter parameters and the high-pass filter parameters; and
   selecting calibrated low-pass filter parameters and high-pass filter parameters in the set of filtering parameters as low-pass filter parameters and high-pass filter parameters in the set of filtering parameters providing a fit of the set of features extracted and/or the classification signal with a reference set of features extracted and/or a reference classification signal.

9. The method of claim 8, wherein the calibrating comprises a genetic algorithm for selecting the calibrated low-pass filter parameters and high-pass filter parameters in the set of filtering parameters.

10. A computer program product loadable in a memory of a processor and comprising software code portions for executing the steps of the method of claim 1 when the computer program product is run on the processor.

11. An electrophysiological signal processing system comprising:
    a electrophysiological signal sensor configured to collect an electrophysiological signal indicative of a level of attention of a human, the electrophysiological signal comprising a PhotoPletysmoGraphy (PPG) signal;
    a processor;
    a non-volatile memory comprising a program to be executed in the processor, the program comprising instructions for:
      filtering the electrophysiological signal via joint low-pass and high-pass filtering using a set of filtering parameters including low-pass filters parameters and high-pass filters parameters having a set of low-pass cut-off frequencies and a set of high-pass cut-off frequencies respectively;
      applying a first artificial neural network processing to the filtered electrophysiological signal to extract therefrom a set of features of the electrophysiological signal;
      applying a second artificial neural network processing to the set of features extracted from the filtered signal to produce a classification signal indicative of the level of attention of the human; and
      generating a trigger signal to trigger a user circuit based on the classification signal.

12. The system of claim 11, wherein the electrophysiological signal further comprises an ElectroCardioGraphy (ECG) signal.

13. The system of claim 11, wherein the set of filtering parameters comprises low-pass and high-pass filters parameters selected from Butterworth, Chebyshev type I, Chebyshev type II and elliptic filter parameters.

14. The system of claim 11, wherein the program comprises further instructions for:
    comparing the classification signal with an attention threshold level, wherein when the classification signal reaches the attention threshold level, the trigger signal is configured to trigger an alert circuit.

15. The system of claim 11, wherein the electrophysiological signal is collected from a driver of a vehicle and the user circuit comprises a user circuit on board the vehicle.

16. The system of claim 15, wherein the electrophysiological signal is collected from the driver of the vehicle via a PhotoPletysmoGraphy (PPG) sensor or an ElectroCardioGraphy (ECG) sensor on board the vehicle.

17. The system of claim 11, wherein the program comprises further instructions for applying artificial neural network processing comprises instructions for applying Scaled Conjugate Gradient Fully Connected layer neural network processing.

18. The system of claim 11, wherein the program comprises further instructions for calibrating the set of filtering parameters, wherein instructions for the calibrating comprises instructions for:
   varying low-pass filter parameters and high-pass filter parameters in the set of filtering parameters, wherein the set of features extracted and/or the classification signal (DS) vary as a function of a variation of the low-pass filter parameters and the high-pass filter parameters; and
   selecting calibrated low-pass filter parameters and high-pass filter parameters in the set of filtering parameters as low-pass filter parameters and high-pass filter parameters in the set of filtering parameters providing a fit of the set of features extracted and/or the classification signal with a reference set of features extracted and/or a reference classification signal.

19. The system of claim 18, wherein instructions for the calibrating comprises a genetic algorithm for selecting the calibrated low-pass filter parameters and high-pass filter parameters in the set of filtering parameters.

20. A vehicle (V) comprising:
   an electrophysiological signal sensor configured to collect an electrophysiological signal indicative of a level of attention of a human, the electrophysiological signal comprising a PhotoPletysmoGraphy (PPG) signal;
   a processor;
   a non-volatile memory comprising a program to be executed in the processor, the program comprising instructions for:
      filtering the electrophysiological signal via joint low-pass and high-pass filtering using a set of filtering parameters including low-pass filters parameters and high-pass filters parameters having a set of low-pass cut-off frequencies and a set of high-pass cut-off frequencies respectively,
      applying a first artificial neural network processing to the filtered electrophysiological signal to extract therefrom a set of features of the electrophysiological signal,
      applying a second artificial neural network processing to the set of features extracted from the filtered signal to produce a classification signal indicative of the level of attention of the human, and
      generating a trigger signal based on the classification signal; and
   a driver assistance device configured to be triggered by the trigger signal.

21. The vehicle of claim 20, wherein the trigger signal is generated within 8 seconds after a time of starting to collect the electrophysiological signal.

* * * * *